United States Patent [19]
Johnston

[11] 4,363,624
[45] Dec. 14, 1982

[54] METHOD OF AFFIXING A DENTAL APPLIANCE

[75] Inventor: Reece W. Johnston, Fort Worth, Tex.

[73] Assignee: Advance Dental Corporation, Fort Worth, Tex.

[21] Appl. No.: 195,661

[22] Filed: Oct. 9, 1980

Related U.S. Application Data

[63] Continuation-in-part of Ser. No. 83,460, Oct. 10, 1979, abandoned, which is a continuation-in-part of Ser. No. 883,408, Mar. 6, 1978, Pat. No. 4,200,980.

[51] Int. Cl.³ ............................................. A61C 7/00
[52] U.S. Cl. ...................................... 433/9; 433/183; 433/219
[58] Field of Search ........................ 433/8, 9, 183, 219

[56] References Cited

U.S. PATENT DOCUMENTS

| | | | |
|---|---|---|---|
| 3,250,003 | 5/1966 | Collito | 32/14 |
| 3,738,005 | 6/1973 | Cohen et al. | 32/14 B |
| 3,955,282 | 5/1976 | McNall | 32/14 C |
| 4,010,545 | 3/1977 | Kilian et al. | 32/14 A |

*Primary Examiner*—Lorenzo B. Hayes
*Attorney, Agent, or Firm*—Wm. T. Wofford; James C. Fails; Arthur F. Zobal

[57] ABSTRACT

A method for affixing a dental appliance to teeth characterized by effecting a layer of bonding resin and catalyst on the teeth, effecting a layer of a substantially uniform admixture of only two reactants of a three-reactant system, the two reactants including the bonding resin and one of the other reactants, on the teeth; effecting a second layer of a substantially uniform admixture of a second two reactants of said three reactant system, said second two reactants including the bonding resin and the other of the reactants, on the dental appliance to be affixed to the teeth; positioning the portion of the dental appliance adjacent the teeth with the bonding resin, catalyst, and initiator in situ to effect polymerization and bonding on the surface of each of the teeth. After a predetermined cure time, the remainder of the dental appliance is affixed. Also disclosed are the preferred bonding resins, catalysts and initiators, as well as the preferred viscosity and fillers for obtaining the desired viscosity; and an indirect bonding method.

17 Claims, 3 Drawing Figures

METHOD OF AFFIXING A DENTAL APPLIANCE

This patent application is a continuation-in-part application of prior U.S. Ser. No. 083,460, now abandoned, filed Oct. 10, 1979, entitled "METHOD OF AFFIXING A DENTAL APPLIANCE"; and itself a continuation-in-part application of prior U.S. Ser. No. 883,408, now U.S. Pat. No. 4,200,980, filed Mar. 6, 1978, entitled "ORTHODONTIC FORMULATION AND METHOD", the same inventor in each of the cases.

FIELD OF THE INVENTION

This invention relates to a method of affixing a dental appliance to teeth. More particularly, this invention relates to a method of bonding directly to the teeth to facilitate affixing a dental appliance thereto.

DESCRIPTION OF THE PRIOR ART

The prior art has seen a wide variety of orthodontic corrective procedures to align mal-occluded teeth. Most of these corrective procedures employed a dental appliance in one way or another to correct improper growth of the teeth. The term "dental appliance" is employed in its broad sense in this application to signify any of the appliances whether to correct the growth of teeth, bridging of the teeth and the like. Such dental appliances typically include braces, space maintainers, elastics, splints, bridge works of more elaborate type and any other type of device that will be affixed to one or more of the teeth in the mouth with the objective of supporting or affecting the action or growth of other teeth.

A major orthodontic corrective procedure to align mal-occluded teeth is the placement of metal bands around individual teeth and thereafter affixing the remainder of the dental appliance to these metal bands. The metal bands may have affixed bases or brackets, sometimes referred to as the appliance, or part thereof. Wires having high-tensile strength are then attached to the metal bands and the fixed portion of the appliance and then to the remainder of the appliance and teeth to affect proper tooth movement through the action of the wire itself or of springs or spurs or elastic bands attached to the appliance. The affixed appliances, or brackets require precise positioning to effect proper tooth movement.

Adhesive bonding of the affixed appliances to tooth surfaces is the ultimate in this type of orthodontic practice in order to eliminate the tedious band fitting procedure and to greatly reduce the decalcification of teeth and the gingival damage that all too frequently occurs with banding. Moreover, bonding with a resin type adhesive facilitates cleaning by the patient with less opportunity for food accumulation and consequent tooth decay compared to the banding because most of the appliances are at the front surface of the teeth in adhesive bonding with greater accessibility for cleaning.

Despite the advantages of adhesive bonding, it has not achieved universal success because of the inconsistent results from the currently availably bonding orthodontic adhesives and the techniques, or methods, of using them.

Currently available orthodontic bonding adhesives generally use one of two techniques for applying orthodontic appliances to the teeth. In each of the techniques the teeth are prepared by cleaning, acid etching, washing and drying.

In the first technique, the bonding resin co-monomer is not mixed with a catalyst but is applied to a clear, transparent plastic bracket that is precisely positioned on the dried tooth surface. An ultraviolet light is directed onto the clear bracket so as to penetrate through to initiate polymerization of the bonding resin. In this way, the viscosity of the resin co-monomer can be adjusted to optimize wetting and avoid creeping; but the requirement for a clear, light-penetrating material for a bracket limits the strength of the bracket. Transparent brackets are generally inferior to the stainless steel brackets otherwise employed. Consequently, there are frequent failures due to inadequate structural strength to resist the stress of the attachment; for example, force by high-tensile strength wire. The ultraviolet light itself, if used indiscriminately, is known to produce skin cancer, especially on soft tissue. Consequently, many orthodontists favor another procedure.

Another procedure comprises admixing the exact proportions of an adhesive formulation consisting of filler, catalyst, co-monomer resin and accelerator, or initiator, on a cold plastic slab, or glass plate and the like. The mixing of the catalyst, accelerator, and co-monomer initiates polymerization of the co-monomer resin immediately so the orthodontist has limited working time to coat the several bases of the brackets, or portion of the appliance to be bonded to the teeth, and to precisely position it on the prepared teeth surfaces. Also, the viscosity of the resin is continuously changing with the degree of polymerization. This affects positioning and creep of the brackets, as well as the ultimate bond strength. Viscosity also varies as the proportions of resin and catalyst are varied, deliberately or carelessly. For example, if the amount of catalyst in relation to the resin is too large, polymerization is too rapid and the higher viscosity of the resulting resin will cause inadequate wetting of the surfaces of the teeth and bracket base. (Good wetting onto clean surfaces is the most important criterion in forming strong bonds). The result is a weak bond at best and ultimate displacement of the appliance from the tooth. On the other hand, if the proportion of catalyst is too small, the resulting mixture prepared by the orthodontist or his assistant has a low viscosity due to slow polymerization. This results in "creeping" of the appliance from its optimum placement position on a respective tooth. If attempts are made to reposition a bracket, or portion of an appliance, after "creep", then the bond is weakened and the appliance will ultimately be displaced from the tooth.

From the foregoing, it can be appreciated, that the prior art has not been totally satisfactory in solving the problems. First, a thorough mixing of exactly the right proportions of the adhesive is a requirement in order to evenly disperse the catalyst. Second, even a properly proportioned admixture forces the orthodontist to work in a limited time frame without the luxury of being able to correct for unanticipated delays or contingencies. Otherwise he must begin anew, with wasting of time and expensive adhesive.

Ideally, a bonding method would have the following features:

1. The bonding method should avoid the use of ultraviolet light or carcinogenic agents.
2. The bonding method should allow relative freedom of the dentist to be as precise in placement and as careful in maintaining the bracket, or base of a dental appliance, in position to avoid creep as he wishes, without having to work within a time constraint.

3. The bonding method should provide a relatively constant viscosity that is optimal for effectively wetting the surfaces of the teeth and of the dental appliance that is to be bonded to the teeth; simultaneously avoiding creep of the bracket, or portion of the dental appliance to be bonded to the teeth.

4. The bonding method should obviate the necessity for careful admixing of predetermined portions so as to be operable even at moments of carelessness by the orthodontist or assistant.

5. In specific embodiment, the bonding method should be operable by either direct bonding or indirect bonding techniques if the latter are desired to speed up the affixing of the dental appliance.

6. Moreover, in specific aspects, the bonding method should provide a means that will facilitate application of only one formulation to the portion of the dental appliance that is to be bonded to the teeth and only one formulation to the tooth, yet produce a final satisfactory bond that is easily removed at the appropriate time.

7. The bonding method and composition should facilitate using complementary advantageous method steps; such as, forming shields or sealant layers, over the teeth to minimize decay.

In my co-pending Application Ser. No. 883,408, filed Mar. 6, 1978, and entitled "ORTHODONTIC FORMULATION AND METHOD", I disclosed an improved method and composition for direct bonding of the dental appliances to teeth that obviated many of the disadvantages of the prior art. It was found, however, that the method of that invention was needlessly complex, as were other related methods, such as disclosed in U.S. Pat. Nos. 3,955,282; 4,010,545; 3,738,005; and 3,250,003.

SUMMARY OF THE INVENTION

Accordingly, it is an object of this invention to provide a bonding method for bonding a dental appliance to teeth that has one or more of the foregoing feature not heretofore provided by the prior art, while alleviating the disadvantages of the prior art.

It is another object of this invention to provide a method for bonding a dental appliance to teeth that has a plurality of the features delineated hereinbefore as desirable and not heretofore provided by the prior art, simultaneously alleviating the disadvantages of the prior art and simplifying the needlessly complex methods thereof.

These and other objects will become clear from the descriptive matter hereinafter, particularly when taken in conjunction with the appended drawings.

In accordance with this invention there is provided a method of affixing a dental appliance to at least one tooth in the mouth comprising for each such tooth a plurality of steps of:

a. effecting on the surface of the tooth to which the dental appliance is to be bonded a layer of a substantially uniform admixture of only a first two reactants of a three-reactant system consisting essentially of the bonding resin, a catalyst and initiator; the first two reactants including the bonding resin and a first one of the other two reactants that will effect polymerization of the bonding resin in the presence of the second other reactant, the surface of the tooth having been cleaned and dried so as to effect a good bond;

b. effecting on a base of at least a portion of the dental appliance that is to be bonded to the tooth, the base having been cleaned and dried so as to effect a good bond, a second layer of a substantially uniform admixture of only a second two of the reactants of the reactant system, the second two reactants including the bonding resin and the second other reactant, the bonding resin being polymerized in the presence of both the other reactants; namely catalyst and initiator;

c. positioning a portion of the dental appliance adjacent the surface of the tooth with the layer of bonding resin, catalyst and initiator disposed between the base and the tooth so as to obtain polymerization of the resin and the necessary bonding of the base of the dental appliance to the teeth;

d. after a predetermined cure time sufficient to obtain curing of the bonding resin, affixing the remainder of the orthodontic appliance.

Specifically, the layer that is placed on the surface of the tooth may include the bonding resin and the catalyst; and the layer that is placed on the base of the portion of the dental appliance, or bracket, may include the bonding resin and the initiator. On the other hand, the layers can be reversed and the bonding resin and initiator applied to the tooth and the bonding resin and the catalyst applied to the base of the dental appliance. It is imperative that only two of the reactants be employed in each layer such that there is an adequate time to work with the unit, yet when all three are brought together you have a complete three reactant system, with or without filler for viscosity control. It is noteworthy that in this embodiment, the bonding resin is provided in each of the layers. In order to keep this already lengthy patent application from becoming unduly long, the discussion hereinafter will be given with respect to including a layer of the bonding resin and catalyst on the tooth and a layer of bonding resin and initiator on the bracket base, although it is to be born in mind that these may be reversed if desired.

In other embodiments, indirect bonding is provided.

In the method of this invention, the bonding resins are selected from classes consisting of epoxy resin, per se, or capped with hydrolysis-resistant moieties such as the acrylic or methacrylic moieties; urethane resin; cyanoacrylate resin; methacrylate resin; vinyl ester resin; and acrylate resin. The filler that is employed to obtain the critical viscosity comprises small particles of alumina, calcium fluoride, glass, asbestos, or silica. The particle sizes are from colloidal sizes up to 35 microns with no particle size large enough to interfere with the bonding.

DESCRIPTION OF THE PREFERRED EMBODIMENTS

Figure 1:
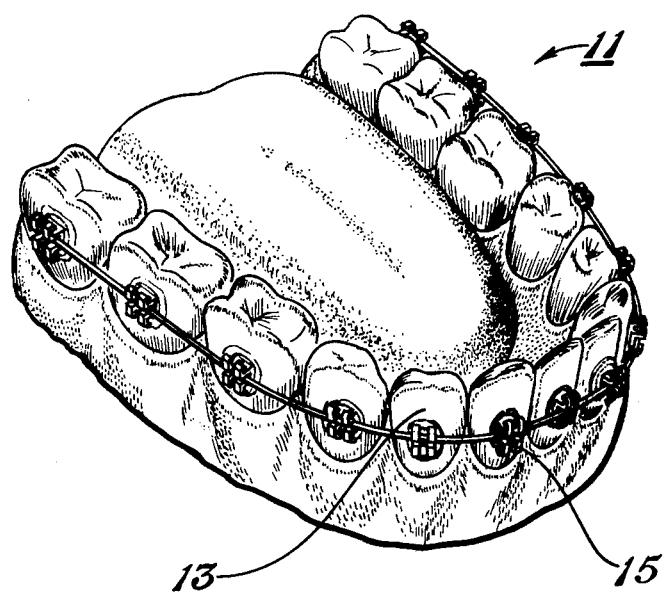
FIG. 1 is an isometric view of a dental appliance bonded to teeth in the mouth.

The descriptive matter immediately hereinafter is arranged so as to describe the materials that have been referred to in respective method steps. Accordingly, the first descriptive matter will be clarifying what is meant by the respective bonding resins and catalysts delineated in the Summary of the Invention hereinbefore.

The bonding resins that are employed in this invention are those resins that will bond in the presence of a catalyst to form a firm, substantially permanent bond that resists hydrolysis, even in the presence of mouth acids and enzymes in the mouth. The bond that is formed, as well as the catalyst and bonding resin should be nontoxic so that the patient is not adversely affected during the bonding of the dental appliance onto the teeth or the retention of the appliance in the mouth. These types of bonding resins are conventionally available and include the epoxy resin, per se, or capped with hydrolysis-resistant moieties; urethane resin; cyanoacrylate resin; methacrylate resin; vinyl ester resin; and acrylate resin. If desired, the resins that have ends that do not resist hydrolysis by their own chemical nature are capped with hydrolysis-resistant moieties such as the acrylate moiety or methacrylate moiety. Both the uncapped resins such as epoxy resins and methacrylic capped epoxy resins are commercially available, as from DuPont, Wilmington, Del.; Dow Chemical Company, Midland, Mich.; Shell Chemical Co.; Houston, Tex.; or Rohm and Haas Chemical Company, St. Louis, Mo. If desired, the resin like the methacrylate capped epoxy resin may have other monomers such as styrene incorporated into its formulation in order to block hydrolysis of the ester linkage by steric hindrance. To ensure complete understanding, the following structural formula is given to amplify the definition of the epoxy resins. These resins are defined by the structural formula I.

The value of n in the structural formula I is selected such that the molecular weight will be in the range of 10,000–300,000, although it may be even higher to obtain the desired viscosity with lesser amount of filler as described hereinafter with respect to the layer on the bracket bases.

The polymerization of these types of bonding resins is ordinarily effected by free radical initiation employing suitable initiators, or accelerators, as well as catalyst.

Typical of the initiators are amines such as N,N-dimethyl-para-toluidine; N,N-dimethylaniline; and cobalt naphthenate. As is recognized, the cobalt naphthenate is ordinarily employed with methyl ethyl ketone peroxide catalyst for the epoxide type resins. The preferred initiator is N,N-dimethyl-p-toluidine.

The catalyst may comprise any of those that are ordinarily employed for polymerizing these type of monomers. The preferred catalyst for this invention is either benzoyl peroxide of methyl ethyl ketone peroxide.

In accordance with this invention, there is no need to mix a powdered catalyst with a resin to form an admixture that changes viscosity and consistency during application. Instead, the layer of bonding resin and initiator, or accelerator, may be formulated to have the desired critical viscosity in the range of 25,000–40,000 centipoises measured to 50° C. This viscosity is unchanging, therefore, the work time of the orthodontist is essentially limitless, since there is no substantial polymerization until the layer of bonding resin and catalyst on the tooth is emplaced contiguous the layer of bonding resin and initiator on the base of the bracket.

In order to obtain the viscosity as defined hereinbe-

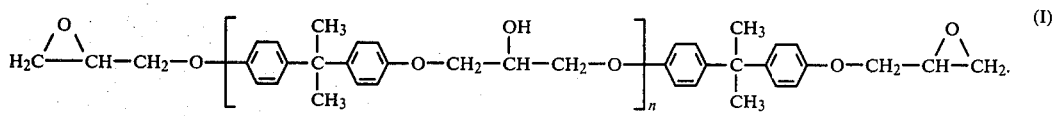

To eliminate the harmful effects of epoxy curing agents the epoxide ends are reacted with the methacrylic moiety shown in formula II.

The methacrylic groups require harmless curing agents to effect polymerization.

Ordinarily, it is preferred to employ monomer additions, or diluents, to obtain clearer, less viscous monomer solutions. These diluents include styrene, methyl methacrylate, hydroxy methyl methacrylate, ethylene glycol dimethacrylate, diethylene glycol dimethacrylate, triethylene glycol dimethacrylate, various polyethylene glycol methacrylates individually, trimethylol propane-trimethacrylate, 1,4-butane glycol dimethacrylate, 1,3-butane glycol dimethacrylate, n-propyl methacrylate, n-butyl methacrylate, penta-erythritol tetra methacrylate, and the like. The preferred resin for bonding is methacrylate capped epoxy diluted with styrene constituting 40–55 percent of the final admixture; but its odor is objectionable. Work is being done to overcome this objection.

Preferably, the bonding resin that is employed with the catalyst in a layer on the teeth will have a low viscosity in the range of 250–5,000 centipoises at room temperature.

fore it is preferred to add an inert filler, in the form of a particulate solid. Preferably, the particles of solid have a predominant size of smaller than 35 microns with no sizes so large as to interfere with proper bonding between the appliance and the teeth. The filler is selected from the group consisting of alumina, barium fluoride, calcium fluoride, glass, asbestos, and silica. Of these, the colloidal silica such as formed by fumed silica is preferable. Thus the optimum viscosity of the bonding resin liquid can be formulated to allow being emplaced intermediate the two layers of catalyst on the appliance and the teeth surfaces that are to be bonded together.

Typically the first layer of the bonding resin and catalyst that is emplaced on the teeth will have a proportion of bonding resin in the range of from 90 percent to 98 percent, the remainder being catalyst.

Typically, the second layer of the bonding resin and the initiator has a concentration in the range of 0.5–3.0 percent by weight of initiator; the optimum concentration of initiator being about 1.5–2.0 percent by weight based on weight of bonding resin and initiator.

The concentration of the filler in the second layer of bonding resin and initiator may vary depending upon the type of filler and bonding resin being employed. With larger filler of, for example, −325 mesh U.S. Standard Sieve, up to 80 percent by weight of filler may be employed. Ordinarily, with colloidal size filler, the concentration of filler will be in the range of 4–10 percent by weight of the bonding resin. The optimum concentration of the filler would be in the range of 6-7 percent of the preferred filler in the preferred resin to obtain the optimum viscosity of about 25,000-40,000 centipoises measured at 50° C.

The cure time is in the range of about 10 minutes to about 2 hours for the bonding strength to develop sufficient strength in the presence of the catalyst and initiator to take the stress attendant to affixing of the remainder of the dental appliance. Ordinarily about 15-20 minutes are allowed before the orthodontist, or dentist, begins to affix the remainder of the dental appliance. In point of fact, the bracket base may be sufficiently adhered to a tooth in as little as 20 seconds to allow moving on to the next teeth. Expressed otherwise, in as little as 20 seconds, the base would be bonded sufficiently to the tooth that the bracket holder can be released and another bracket emplaced contiguous, or adjacent, another tooth with the layers of bonding resin, catalyst and initiator therebetween.

Ordinarily, an orthodontic appliance may comprise a series of mounting brackets that are to be bonded directly to the surfaces of the teeth and the remainder of the appliances high strength wire, connecting the brackets in a manner so as to apply torque or forces to the teeth to effect the desired movement of the teeth. The bases of the brackets are bonded to the teeth by one of two methods preparatory to affixing the remainder of the dental appliance. The first is referred to as direct bonding. The second is referred to as indirect bonding and is employed to expedite affixing the dental appliance to the teeth.

In direct bonding, the method of this invention is performed independently for each tooth involved. A multiplicity of steps is involved for each of the surfaces of the teeth to which a particular and respective bracket is to be bonded. For each tooth to be treated, the method comprises the steps of:

a. cleaning the surface of the tooth to which the bracket is to be affixed;
b. acidizing the surface of the tooth to which the bracket is to be affixed to create an etched surface;
c. water washing the acid-etched surface of the tooth to insure it has been thoroughly cleaned;
d. drying the tooth with clean warm air;
e. applying the first layer of bonding resin and catalyst to the cleaned, etched, dried tooth surface;
f. applying to the cleaned, dried base of the bracket a second layer of catalyst and initiator;
g. positioning the bracket base adjacent the surface of the tooth with the intermediate layer of the bonding resin, catalyst and initiator so as to obtain polymerization of the bonding resin and the necessary bonding of the bracket to the tooth;
h. repeating the above described steps for each of the several teeth involved;
i. after a predetermined cure time, affixing the remainder of the dental appliance to the brackets.

Figure 2:
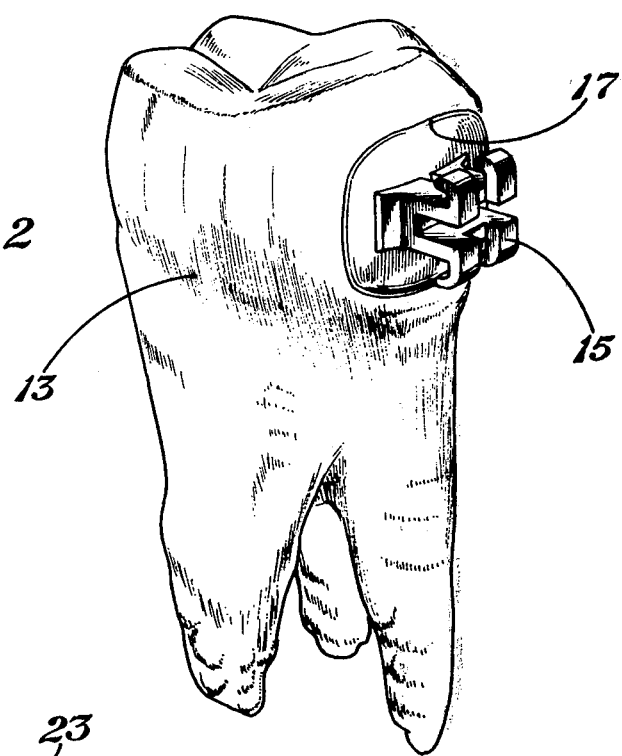
FIG. 2 is an isometric of a tooth having a bracket bonded thereto in accordance with FIG. 1.
Figure 3:
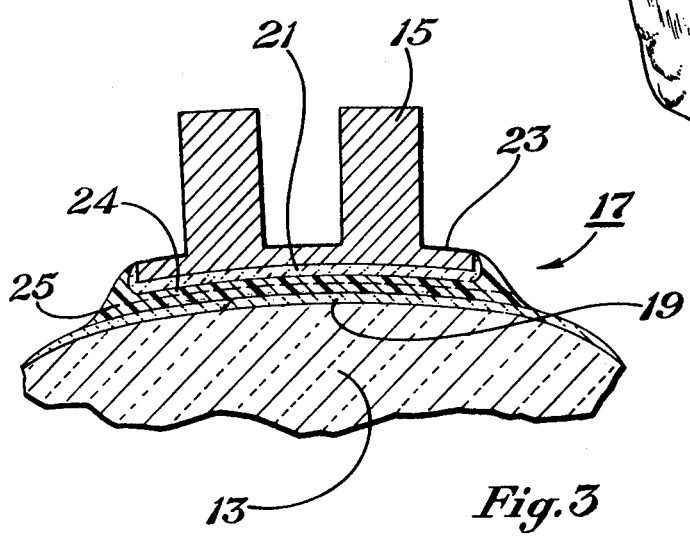
FIG. 3 is a partial cross sectional view of the base of the bracket bonded to the surface of the tooth.

The method steps may be understood completely by referring to the accompanying FIGS. 1-3 in conjunction with the following descriptive matter.

FIG. 1 illustrates a dental appliance 11 applied to the teeth 13 by way of brackets 15. Each of the bases of the brackets are adhered to the surface of the respective teeth by durable bond 17, FIG. 2. The bond 17, FIG. 3, is formed by polymerization reaction between the first layer 19 of bonding resin and catalyst on the surface of the tooth 13 and a second layer 21 of catalyst and initiator on the base 23 of the bracket 15. At the interface, denoted by dashed line 24, the polymerization reaction expands rapidly, as shown by the intermediate layer 25. Finally, through molecular diffusion of the bonding resin, catalyst and initiator in the combined layer, a final bond 17 is formed, presumably by the mechanism of free-radical polymerization.

The component of low viscosity consisting of bonding resin and catalyst (or initiator substituted for the catalyst) is applied to both the cleaned, dried tooth surface and to the cleaned base of the bracket; the second component of high viscosity bonding resin containing the initiator (or catalyst substituted therefor) and filler is applied onto the layer already present on the base of the bracket, then the bracket is immediately applied to the layer of the first component on the tooth.

In carrying out the method of the invention, the dentist, the orthodontist, or the assistant first cleans the teeth with a suitable material such as a pumice type material in the form of a toothpaste or the like. Such pumices and pastes are conventionally employed and need not be described in great detail herein. The pumice type paste is then washed from the teeth with water and the teeth dried by warm clean dry air. Next an acid etch is applied to the teeth. Ordinarily phosphoric acid having a concentration in the range of 30-50 percent by weight is dabbed onto the teeth with a cotton pellet or light brush. After about a minute and a half, the teeth are rinsed with water again and dried with warm clean dry air. Next the cleaned metal brackets are arrayed on an absorbent towel. Preferably, a bracket is selected to have a curvature of the base to match the curvature of the surface of the tooth to which it will be adhered. As indicated hereinbefore, the bases of the respective brackets will have been cleaned of all dirt and grease. The grease is particularly detrimental to the effecting of a durable bond by the resin, since it limits the bonding to the surfaces.

A relatively thin layer of the bonding resin and catalyst is applied to the surface of the teeth to which the brackets are to be affixed, or bonded. As indicated hereinbefore, the bonding resin applied to the teeth has a lower viscosity in the range of 250-5,000 centipoises at room temperature. There is very little interaction between the catalyst and the bonding resin in the absence of an initiator, or accelerator. To promote polymerization as rapidly as possible but within the time frame permitted, the bonding resin and catalyst are also applied to the base of the bracket followed by a second layer of higher viscosity bonding resin, initiator and filler.

The bonding resin having the proper amount of viscosity to prevent "creep" and the initiator are admixed together and are applied to the bases of the brackets so as to form a second layer of substantially uniform admixture thereon. Preferably a desired amount of filler is included in the second layer to obtain the desired viscosity in the delineated range.

The respective uniform admixtures of, respectively, the bonding resin and catalyst and, the bonding resin and initiator and filler (if employed) may be separate prepared admixtures specifically available commercially for bonding the bracket to the teeth. Typical such prepared admixtures are readily available, as from Advance Dental Corporation, Fort Worth, Tex.

Specifically, the relatively low viscosity solution of the bonding resin and catalyst may be brushed onto the teeth and bracket, or splayed onto the teeth and bracket with a syringe or the like. The second, more viscous layer of the bonding resin and the initiator can be emplaced on the bases of the brackets with a spatula or dispensing device such as a syringe, tube or the like. Thereafter, each bracket is positioned on its tooth in the exact location desired. One advantage of this invention is that it is unnecessary to hold the bracket firmly in place as required heretofore. The close contact effects molecular interdiffusion such that there is a mixture of the bonding resins, catalyst and initiator to provide rapid polymerization and finally bonding. For all practical purposes, because of the viscosity of the resin, the bracket will remain in place without creeping as soon as it has been firmly emplaced. This is one advantages of this invention—that the orthodontist does not have to waste time holding a bracket until a conventional adhesive builds sufficient gel strength to hold the bracket in place. The next and subsequent brackets are then similarly treated and applied to the other teeth.

During the emplacement of the brackets, a small amount of the bonding resin catalyst and initiator is ordinarily extruded from between the bracket base and the tooth surface around the edge of the bracket. This cement, or bonding resin, is preferably folded over and around the edge of the bracket for better mechanical locking in place.

In accordance with this invention, it has been found that the simple expedient of employing only two solutions will effect a durable bond within about ten to twenty minutes sufficient to allow attaching the remainder of the dental appliance. The thin layer of resin occupies very little space between the bracket and the tooth; and, because of the relatively small mass, there is rapid polymerization, producing strong bonds and consistent results; in contrast to the prior art methods.

The affixing of the remainder of the dental appliance is carried out by wiring with the high strength wires as has been done for many years and need not be described in great detail herein. Similarly, adjustments are made as conventional.

In the final step, when the orthodontic appliance is ready to be removed, the orthodontist may unwire the remainder of the appliance and employ snub-nosed gripper pliers to shear through the cement formed by the cured bonding resin. One of the advantages of this invention is that only about 5 percent of the bonding resin remains on the teeth; whereas with a conventional mixture about 50 to 100 percent remains on the teeth. The total effect of this small residue is that much less time has to be spent polishing off the cement, or cured bonding resin, from the teeth with this invention.

In the indirect bonding of the dental appliance to the teeth, a cast is made of the mouth of the patient and the brackets are temporarily affixed into the desired position onto the cast. A layer of soft plastic such as polyethylene is folded over the brackets and vacuum drawn into place so as to embed the brackets in the soft plastic. Thereafter, the soft plastic containing the brackets is folded back and the embedded brackets are cleaned of the material used to temporarily affix the brackets to the cast teeth.

A layer of bonding resin and catalyst is effected on the clean dry teeth, similarly as described hereinbefore. Similarly as described hereinbefore, a layer of bonding resin and initiator is effected on the bases of brackets. The plastic with the brackets embedded therein is inserted into the patients mouth such that the bracket bases are suitably emplaced adjacent the surfaces of the teeth to which they will bond. The plastic with the brackets emplaced is left in the patients mouth for a suitable interval of time to bond the brackets to the teeth. This time will be a short time of from only a few minutes to as much as ten to twenty minutes. Thereafter, the plastic is removed to leave the brackets in place on the teeth in the patients mouth. This technique is employed for speed in applying the brackets.

After the cure time of ten to twenty minutes, the remainder of the dental appliance can be affixed. Adjustments and finally removal are carried out as described hereinbefore.

The following examples are given to illustrate in a very specific way this invention.

EXAMPLE I

In this example the orthodontist first cleaned the teeth with a pumice type toothpaste and water, and wiped clean only with cotton pellet. Thereafter, the orthodontist etched the teeth with a 37.5% solution of phosphoric acid. This solution was debbed carefully onto the teeth with cotton pellets. This effected a clean acid etch. After allowing about one and a half minutes, the acid was thoroughly rinsed from the teeth and the teeth were again dried with dry air.

A first layer was formed on the teeth by brushing thereonto a substantial uniform admixture of monomer resin and catalyst. Another layer of the same material was brushed onto the base of the bracket. The monomer resin was methacrylate-capped epoxy resin containing styrene and having a viscosity of about 500 centipoises at 77° F. The catalyst was benzoyl peroxide.

The bracket bases had applied to them a second layer of bonding resin and the initiator. The bonding resin contained 1.2% by weight initiator and 6.7% by weight a filler. The initiator was N,N-dimethyl-p-toluidine. The filler was fumed colloidal silica, Cabosil from Cobot Corp., Billerica, Mass. The resin employed was a methacrylate-capped epoxy resin containing styrene amounting to about 45% of the mixute. The admixture had the desired viscosity of about 32,000 centipoises measured at 50° C. The admixture was applied by spatula to the base of each metal bracket.

Each metal bracket was firmly affixed to each tooth by means of tweezers, applying a firm force against each bracket in the exact position desired. After placement of the bracket on the tooth, the resin held the bracket in the position without allowing the bracket to creep. The excess bonding resin that was exuded from between the base of the bracket and the tooth was folded around the edge of the bracket with a small spatula.

The remaining brackets were applied in the same manner.

Sufficient curing time was allowed; for example about 20 minutes; and the remainder of the appliance was affixed into place against each of the brackets to apply the desired force to affect the movement of the teeth in the desired way.

The orthodontist was thereafter able to make adjustments on the appliances that were applied to pull the teeth into the position desired. The teeth may be pushed or pulled with this method by using an external appliance.

When ready to be removed, the orthodontist employed snub-nosed gripper pliers and sheared through the cement formed by the cured resin. Only about 5% of the total cement remained in place on the teeth. This cement was polished from the teeth and no ill effects were observed.

EXAMPLE II

The same procedure and steps were carried out in this example as were carried out in Example I except that the methacrylate capped epoxy resin contained diluent monomers other than styrene. One reactive diluent monomer was substituted for styrene in a series of resins with different reactive diluent monomers. For example reactive diluents used in the series were methyl methacrylate, hydroxy methyl methacrylate, ethylene glycol dimethylacrylate, diethylene glycol dimethacrylate, triethylene glycol dimethylacrylate, various polyethylene glycol methacrylates individually, trimethylol propane-trimethacrylate, 1,4-butane glycol dimethacrylate, 1,3-butane glycol dimethacrylate, n-propyl methacrylate, n-butyl methacrylate, penta-erythritol tetramethacrylate, and a few other methacrylate monomers. Each of these resins was found to provide a satisfactory bonding job.

While the method of this invention has been described hereinbefore directed primarily to the practice of orthodontia, it should be remembered that it may be employed for adhering directly to the teeth other dental appliances or the like. Specifically, such things as metal crowns, protective sheaths, space maintainers, bridges, peridontal splints, and other such dental appliances of a similar nature may be adhered directly to the teeth through the use of the respective layers of bonding resin and initiator on the respective tooth and dental appliance.

Having thus described the invention, it will be understood that such description has been given by way of illustration and example and not by way of limitation, reference for the latter purpose being had to the appended claims.

I claim:

1. A method of affixing a dental appliance to at least one tooth, comprising the steps of:
    a. effecting on a predetermined etched and dried surface of the tooth to which a portion of a dental appliance is to be bonded a first layer of a substantially uniform admixture of two reactants of a three-reactant system consisting essentially of a bonding resin that is hydrolysis resistant, that is partially polymerized and that will polymerize further in the presence of a catalyst and an initiator to bond in the presence of acids and enzymes in the mouth and selected from the class consisting of epoxy resin, urethane resin, methacrylate resin, vinyl ester resin, and acrylate resin; a catalyst that will affect polymerization of said bonding resin and selected from the class consisting of benzoyl peroxide, and methyl ethyl ketone peroxide; and an initiator selected from the class consisting of N,N-dimethyl-para-toluidine, N,N-dimethyl aniline, and cobalt naphthenate; said two reactants including said bonding resin and either one said catalyst or initiator that will affect polymerization of said bonding resin;
    b. effecting on a cleaned and dried surface of at least a portion of a dental appliance that is to be bonded to said tooth, a proper viscosity second layer of a substantially uniform admixture of two reactants of said three-reactant system, said two reactants including said bonding resin and the other of said initiator or said catalyst; and said bonding resin being polymerized by said second other reactant in the presence of said first other reactant; and
    c. positioning said at least a portion of said dental appliance adjacent said surface of said tooth wherein said two layers containing said bonding resin, catalyst and initiator are brought together to obtain polymerization of said bonding resin and hence the necessary bonding of said at least a portion of the dental appliance to the surface of the tooth; said proper viscosity being obtained by a filler added to said second layer to obtain the desired viscosity of said resin, to avoid creep and to obtain the desired wettability of said tooth to said three reactants.

2. The method of claim 1 wherein said two reactants of said first layer on said tooth comprises said bonding resin and said catalyst that will effect polymerization of the bonding resin in the presence of said initiator; and said second layer comprises said bonding resin and said initiator that will effect polymerization of said bonding resin in the presence of said catalyst.

3. The method of claim 2 wherein said proper viscosity of said second layer of said resin and accelerator is a viscosity in the range of 25,000–40,000 centipoises measured at 50° C. temperature.

4. The method of claim 3 wherein said second layer has an optimum viscosity of about 32,000 centipoises measured at 50° C.

5. The method of claim 1 wherein said filler is selected from a group consisting of alumina, calcium fluoride, barium fluoride, glass, asbestos, and silica; said filler being in the form of particles that are predominantly in a size up to 35 microns and have no size so large as to interfere with the bonding of said at least a portion of said dental appliance to said tooth.

6. The method of claim 5 wherein said filler is colloidal silica.

7. The method of claim 6 wherein said colloidal silica comprises fumed silica and is present in the concentration in the range of 6–7 percent by weight, inclusive.

8. The method of claim 5 wherein said filler is present in the concentration in the range of 4–10 percent by weight.

9. The method of claim 1 wherein said bonding resin is selected from the class consisting of partially polymerized methacrylate resin and acrylate resin.

10. The method of claim 1 wherein said catalyst is benzoyl peroxide.

11. The method of claim 1 wherein said initiator is selected from the class consisting of N,N-dimethyl-p-toluidine, N,N-dimethylaniline.

12. The method of claim 11 wherein said initiator is present in the concentration within the range of 0.5–3.0 percent by weight.

13. The method of claim 1 wherein said first layer of said substantially uniform admixture is applied to both said tooth and said bracket before said proper viscosity second layer of said substantially uniform admixture is applied to said bracket.

14. The method of claim 1 wherein said dental appliance is affixed to brackets that are affixed to the respective surfaces of a plurality of teeth and a plurality of respective said brackets are affixed to each of a plurality of respective said teeth by the steps of:
    a. cleaning the surface of the tooth to which said bracket is to be affixed;
    b. acidizing the surface of said tooth to which said bracket is to be affixed to create a cleanly etched surface;

c. rinsing the acid etched surface of said tooth to insure that it has been water washed and thoroughly cleaned;

d. drying said tooth with clean air;

e. applying to the surface of said tooth a layer of said bonding resin and said catalyst that will polymerize said resin in the presence of an initiator;

f. cleaning and drying the base of said bracket;

g. applying to the cleaned, dried base of said bracket a proper viscosity layer of substantially uniform admixture of said bonding resin that will polymerize in the presence of said initiator and said catalyst and said initiator that will effect polymerization of said bonding resins in the presence of said catalyst;

h. positioning said bracket adjacent said surface of said tooth with the intermediate layers of bonding resin containing said catalyst and said initiator so as to obtain polymerization of the bonding resin and the necessary bonding of the bracket to the tooth; and i. after a predetermined cure time, affixing the remainder of said dental appliance to said brackets.

15. The method of claim 14 wherein said layer of bonding resin and catalyst in accordance with step e, is applied to the cleaned and dried base of said bracket following step f. and before step g.

16. A method of affixing a dental appliance to teeth; said dental appliance including both brackets that are to be affixed to said teeth and the remainder of said dental appliance, and said brackets are affixed to said teeth by indirect bonding comprising a plurality of steps of:

a. making a cast of the teeth and mouth of the patient;

b. temporarily arranging the brackets on said cast;

c. folding over said brackets a layer of soft plastic and embedding said brackets in said plastic;

d. removing said plastic and brackets and applying to the clean bracket bases a proper viscosity layer of a substantially uniform admixture of two reactants of a three-reactant system consisting essentially of a bonding resin that is hydrolysis resistant, that is partially polymerized and that will polymerize further in the presence of a catalyst and an initiator to bond in the presence of acids and enzymes in the mouth and selected from the class consisting of epoxy resin, urethane resin, methacrylate resin, vinyl ester resin, and acrylate resin; a catalyst that will affect polymerization of said bonding resin and selected from the class consisting of benzoyl peroxide, and methyl ethyl ketone peroxide; and an initiator selected from the class consisting of N,N-dimethyl-para-toluidine, N,N-dimethyl aniline, and cobalt naphthenate; said two reactants including said bonding resin and either one of said initiator or catalyst that would effect polymerization of said bonding resin;

e. applying to the surfaces of said teeth after said teeth have been cleaned and dried, a substantially uniform admixture of two reactants of said three-reactant system; said second two reactants including said bonding resin and the other of said catalyst or initiator that would effect polymerization of said bonding resin;

f. inserting said plastic with said brackets in place and with said resin, catalyst and initiator intermediate said bases of said brackets and said teeth such that said brackets are emplaced adjacent the surface of said teeth and polymerization of said bonding resin is effected to adhere said brackets on to said teeth, and leaving said plastic in place for a period of at least several minutes to twenty minutes;

g. removing said plastic to leave said brackets in place on said teeth with said brackets bonded directly to said teeth; and h. allowing sufficient time for cure of said bonding resin and thereafter affixing the remainder of said dental appliance.

17. The method of claim 16 wherein said first two reactants comprise said bonding resin and said initiator; and said second two reactants comprise said bonding resin and said catalyst such that when the two layers are brought together all three reactants of said three-reactant system are available for effecting polymerization of said bonding resin and bonding of said dental appliance to said teeth.

* * * * *